United States Patent
Inoue et al.

[11] Patent Number: 5,965,738
[45] Date of Patent: Oct. 12, 1999

[54] PROCESS FOR PRODUCING N-BIPHENYLMETHYLTHIADIAZOLINE DERIVATIVE OR SALT THEREOF AND INTERMEDIATE FOR PRODUCING THE SAME

[75] Inventors: Satoshi Inoue; Nobuya Sakae; Masaharu Yokomoto; Kouji Nishimura; Terukage Hirata, all of Hiroshima, Japan

[73] Assignee: Wakunaga Seiyaku Kabushiki Kaisha, Osaka, Japan

[21] Appl. No.: 08/793,806

[22] PCT Filed: Sep. 19, 1995

[86] PCT No.: PCT/JP95/01866

§ 371 Date: Mar. 20, 1996

§ 102(e) Date: Mar. 20, 1996

[87] PCT Pub. No.: WO96/09301

PCT Pub. Date: Mar. 28, 1996

[30] Foreign Application Priority Data

Sep. 20, 1994 [JP] Japan ................................... 6-224439
Dec. 21, 1994 [JP] Japan ................................... 6-318131

[51] Int. Cl.⁶ ............................................. C07D 285/12
[52] U.S. Cl. ................................................. 548/138; 548/139
[58] Field of Search .................................... 548/139, 138

[56] References Cited

U.S. PATENT DOCUMENTS 5,389,660  2/1995  Greenlee et al. ........................ 514/381

(List continued on next page.)

FOREIGN PATENT DOCUMENTS 0 455 423  11/1991  European Pat. Off. .

(List continued on next page.)

OTHER PUBLICATIONS

David M. Rackham, et al., Organic Magnetic Resonance, vol. 14, No. 6, pp. 515–516, "C NMR Spectra of 1,3,4-Thiadiazole/Thiadiazoline Isomeric Pairs", 1980.

(List continued on next page.)

*Primary Examiner*—Johann Richter
*Assistant Examiner*—Joseph Murray
*Attorney, Agent, or Firm*—Oblon, Spivak, McClelland, Maier & Neustadt, P.C.

[57] ABSTRACT

Described is a process for producing an N-biphenylmethylthiadiazoline derivative (7) in accordance with the reaction formula described below. According to the process of the present invention, it is possible to produce a compound (7) advantageously from the industrial viewpoint.

10 Claims, No Drawings

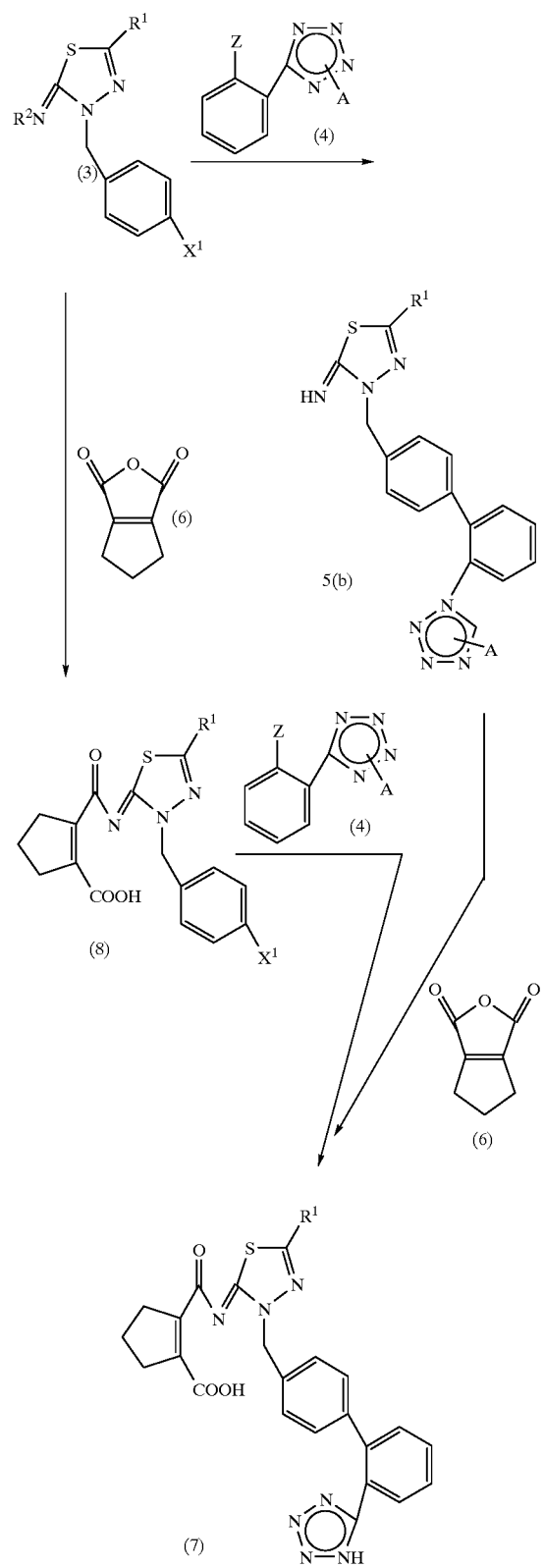

U.S. PATENT DOCUMENTS

| | | | |
|---|---|---|---|
| 5,434,167 | 7/1995 | Ferrari et al. | 514/381 |
| 5,654,322 | 8/1997 | Hirata et al. | 514/363 |

FOREIGN PATENT DOCUMENTS

| | | |
|---|---|---|
| 0 497 150 | 8/1992 | European Pat. Off. . |
| 0 539 086 | 4/1993 | European Pat. Off. . |
| 0 656 355 | 6/1995 | European Pat. Off. . |
| 0 744 402 | 11/1996 | European Pat. Off. . |
| 4218157 | 12/1993 | Germany . |
| WO 92/16524 | 10/1992 | WIPO . |
| WO 93/10106 | 5/1993 | WIPO . |
| WO 93/24474 | 12/1993 | WIPO . |
| WO 94/03435 | 2/1994 | WIPO . |
| WO 94/07483 | 4/1994 | WIPO . |
| WO 95/17396 | 6/1995 | WIPO . |

OTHER PUBLICATIONS

John W. Ellingboe, et al., Journal of Medicinal Chemistry, American Chemical Society, vol. 37, No. 4, pp. 542–550, "Pyrido [2,3,—D]Pyrimidine Angiotensin II Antagonists", 1984.

PROCESS FOR PRODUCING N-BIPHENYLMETHYLTHIADIAZOLINE DERIVATIVE OR SALT THEREOF AND INTERMEDIATE FOR PRODUCING THE SAME

TECHNICAL FIELD

The present invention relates to a process for producing an N-biphenylmethylthiadiazoline derivative or salt thereof which is useful as a therapeutic agent for circulatory diseases such as hypertension, heart diseases or cerebral apoplexy; and to an intermediate for producing the derivative or salt.

BACKGROUND ART

Angiotensin II is an active center of the renin-angiotensin system, and has powerful vasopressor action and stimulating action for the synthesis and secretion of aldosterone in the adrenal cortex. It is also known to be a substance causing hypertension. Its action is considered to be caused through a specific receptor on various target organs such as adrenal cortex, kidneys, arterioles and the peripheries of sympathetic nerves.

Known conventional examples of substances which show antihypertensive effects by pharmacological inhibition of the renin-angiotensin system include angiotensin-converting enzyme inhibitors such as captopril and enarapril, angiotensin II antagonists and renin inhibitors. As angiotensin II antagonist out of these, saralasin ([Sar1, Ala8] AGII), which is an angiotensin II type peptide, and nonpeptide derivatives such as imidazole derivatives (Japanese Patent Laid-Open Nos. SHO 56-7103 and SHO56-71074, and Japanese Language Laid-Open Publication No. HEI 3-501020) and pyrazole derivatives (Japanese Patent Laid-Open No. HEI 3-218371) are already known.

The peptide derivatives, however, have difficulty in clinical applications because of their short in vivo half-life, lack of effectiveness upon oral administration and significant agonistic activities. Among the nonpeptide derivatives, few drugs have been used clinically.

With a view toward providing a clinically excellent drug under such circumstances, the present inventors have carried out an extensive investigation. As a result, finding that an N-biphenylmethylthiadiazoline derivative represented by the below-described formula (7) or salt thereof has an excellent angiotensin II antagonistic action and are useful as therapeutics for circulatory diseases such as hypertension, heart diseases and cerebral apoplexy, the present inventors have already filed international patent application thereon (WO94/04516).

(7)

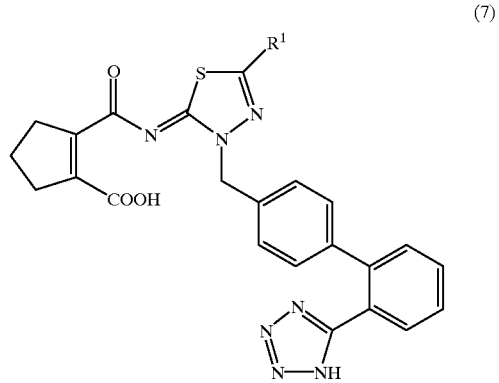

In that international application, an N-biphenylmethylthiadiazoline derivative (7) is prepared in accordance with the process as shown by the following reaction scheme.

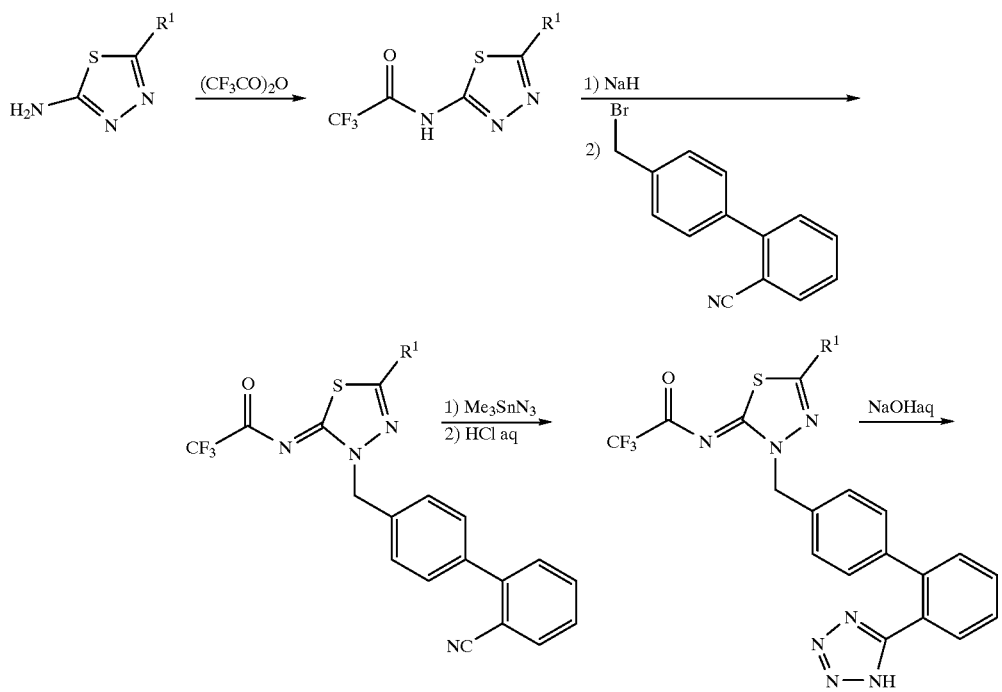

-continued

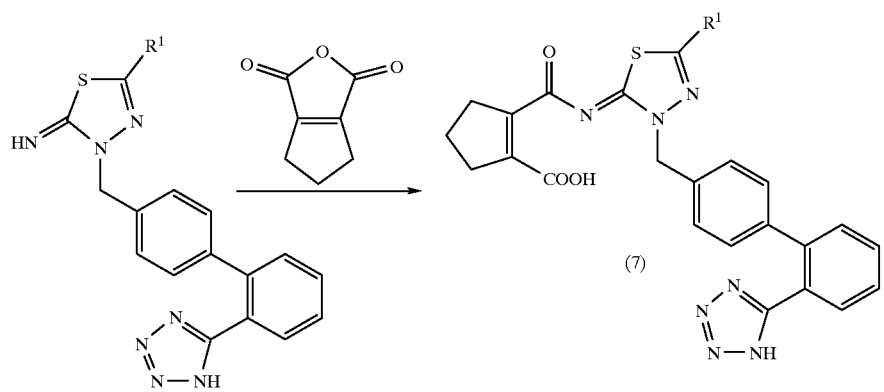

wherein R[1] represents a lower alkyl group.

The above process is however accompanied with the drawback that it includes a step of introducing a tetrazole group into a biphenylnitrile derivative in a manner known to date (Japanese Patent Laid-Open No. SHO 63-23868) so that a harmful trialkyltin compound should be used as a reagent for tetrazole introduction. The above process is therefore not fully satisfactory from the industrial viewpoint.

An object of the present invention is therefore to provide an industrially useful process for producing an N-biphenylmethylthiadiazoline derivative (7) or salt thereof which is an angiotensin antagonist, and also an intermediate for producing the same.

DISCLOSURE OF THE INVENTION

With the forgoing in view, the present inventors have carried out an extensive investigation on the process for producing an N-biphenylmethylthiadiazoline derivative (7) or salt thereof. As a result, it has been found that according to the production process through the novel compound (3a) or (3b), which will be described later, an N-biphenylmethylthiadiazoline derivative (7) or salt thereof can be prepared advantageously from the industrial viewpoint, leading to the completion of the invention.

A process for producing an N-biphenylmethylthiadiazoline derivative (7) or salt thereof according to the present invention is represented by the following reaction scheme:

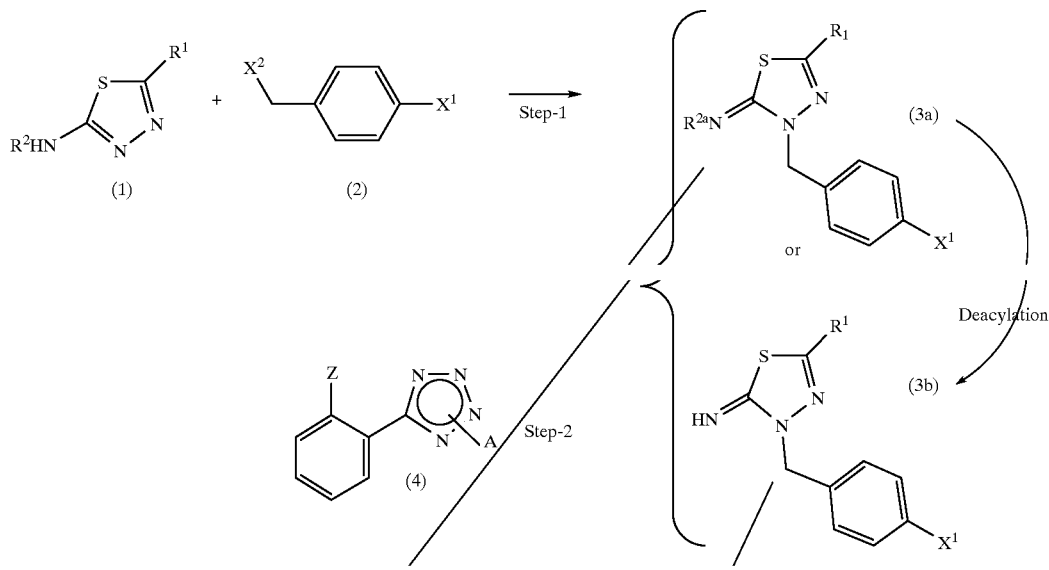

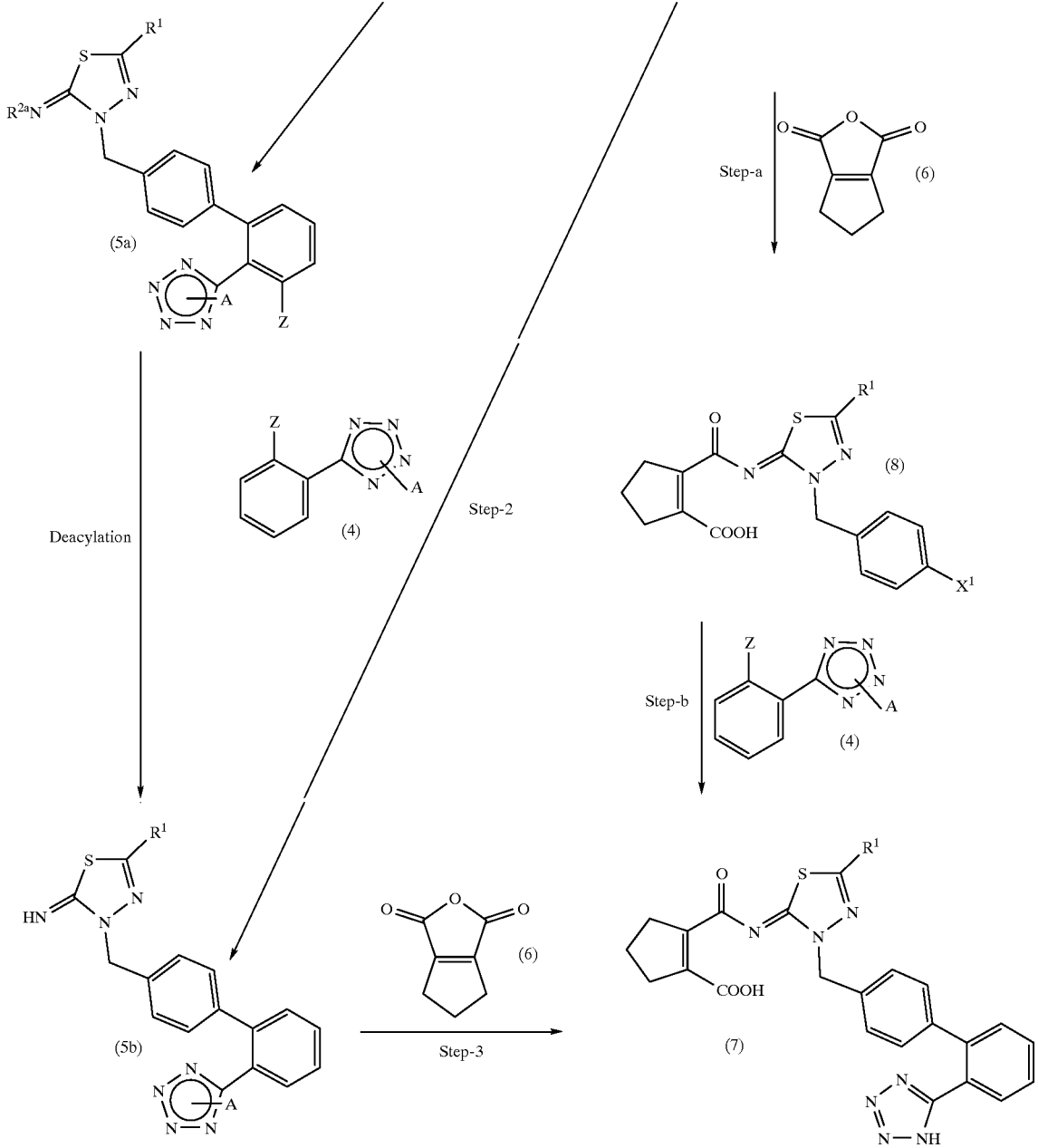

wherein $R^1$ represents a lower alkyl group, $R^2$ represents a hydrogen atom or an acyl group, $R^{2a}$ represents an acyl group, $X^1$ represents a halogen atom, $X^2$ represents a halogen atom or a group $-SO_3R^3$ in which $R^3$ represents an alkyl or aryl group, Z represents a hydrogen atom, a copper atom, a lithium atom, a halogenated metal or a group $-B(OR^4)_2$ in which $R^4$ represents a hydrogen atom or a lower alkyl group, and A represents a hydrogen atom or a tetrazolyl protective group.

The present invention therefore provides a process for producing an N-biphenylmethylthiadiazoline derivative (7) or salt thereof by using as a raw material an N-benzylthiadiazoline derivative (3a) or (3b), the former (3a) being available by the reaction between an aminothiadiazole derivative (1) and a halogenotoluene derivative (2) and the latter (3b) being available by the deacylation of the reaction product, reacting the reaction product or deacylated product with a compound (4) to obtain a compound (5a) or compound (5b), eliminating the acyl group to obtain the compound (5b) in the case where the compound (5a) is obtained, reacting the resulting compound (5b) with a compound (6), and eliminating the tetrazolyl protective group as needed.

The present invention also provides a process for producing an N-biphenylmethylthiadiazoline derivative (7) or salt thereof by reacting the above-described N-benzylthiadiazoline derivative (3b) with the compound (6) to obtain a compound (8), reacting the compound (8) with the compound (4), and then eliminating the tetrazolyl protective group as needed.

The N-benzylthiadiazoline derivatives (3a) and (3b), that is, the compounds represented by the below-described formula (3), and acid salts thereof are novel compounds which have not been reported in literatures and the present invention also provides these compounds and a process for producing them.

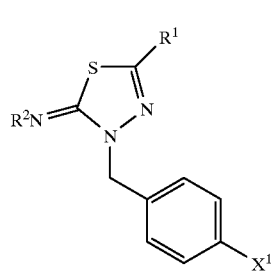

(3)

Best Modes for Carrying Out the Invention

In the present invention, the term "lower" as used for the description of each substituent in each chemical formula means a linear or branched $C_{1-7}$, preferably $C_{1-5}$ substituent.

In the above-described reaction scheme, examples of the lower alkyl group represented by $R^1$ include methyl, ethyl, n-propyl, isopropyl, n-butyl, t-butyl and n-pentyl groups, with an ethyl group being preferred.

Examples of the acyl group represented by $R^2$ or $R^{2a}$ include lower alkanoyl, lower alkenoyl, lower alkoxycarbonyl and lower aralkyloxycarbonyl groups.

Examples of the lower alkanoyl groups include $C_{1-10}$ alkanoyl groups such as formyl, acetyl, propionyl, butyryl, valeryl, isovaleryl, pivaloyl, hexanoyl, heptanoyl, octanoyl and nonaloyl; halo-lower alkanoyl groups such as chloroacetyl, bromoacetyl, dichloroacetyl, trifluoroacetyl, chloropropionyl and tetrafluoropropionyl; hydroxy-lower alkanoyl groups such as hydroxyacetyl, dihydroxyacetyl, hydroxypropionyl and hydroxybutyryl; alkoxy-lower alkanoyl groups such as methoxyacetyl, ethoxyacetyl, methoxypropionyl and ethoxypropionyl; and cyano-lower alkanoyl groups such as cyanoacetyl, cyanopropionyl and cyanobutyryl. Preferred is a trifluoroacetyl group.

Examples of the lower alkenoyl groups include acryloyl, methacryloyl, crotonoyl and pentenoyl groups.

Examples of the lower alkoxycarbonyl groups include methoxycarbonyl, ethoxycarbonyl, propoxycarbonyl, n-butoxycarbonyl and t-butoxycarbonyl groups.

Examples of the lower aralkyloxycarbonyl groups include benzyloxycarbonyl and phenethyloxycarbonyl groups.

Examples of the halogen atom represented by $X^1$ or $X^2$ include fluorine, chlorine, bromine and iodine atoms, with bromine and iodine atoms being preferred.

As $R^3$ of the group —$SO_3R^3$ represented by $X^2$, examples of the alkyl groups include methyl, ethyl and propyl groups and that of the aryl groups include tolyl and phenyl groups.

Examples of the halogenated metal represented by Z include —ZnCl, —MgCl, —CuCl, —BCl$_2$, —ZnBr, —MgBr, —CuBr and —BBr$_2$ groups. Examples of —B(OR$^4$)$_2$ group include —B(OH)$_2$ and —B(OCH$_3$)$_2$ groups.

Examples of the tetrazolyl protective groups represented by A include t-butyl, triphenylmethyl, 2-tetrahydropyranyl, methoxymethyl and ethoxymethyl groups.

The target compounds (7) of the present invention can be converted into pharmacologically acceptable base addition salts thereof. Examples of the base salts include (a) salts with an alkali metal such as sodium or potassium, (b) salts with an alkaline earth metal such as calcium or magnesium, (c) ammonium salts, (d) salts with a nitrogen-containing organic base such as trimethylamine, triethylamine, tributylamine, pyridine, N,N-dimethylaniline, N-methylpiperidine, N-methylmorpholine, diethylamine, cyclohexylamine, procaine, dibenzylamine, N-benzyl-β-phenethylamine, 1-ephenamine or N,N'-dibenzylethylenediamine. Among them, potassium salts are preferred, with dipotassium salts being particularly preferred.

The target compounds (7) of the present invention may be not only in unsolvated forms but also in hydrated or solvated forms. The compounds according to the present invention therefore embrace those in any crystalline forms and their hydrated and solvated products.

Furthermore, the compounds (7) of the present invention include those containing an asymmetric carbon atom so that they can exist as optically active substances. These optically active substances and optically inactive substances are also embraced in the compounds of the present invention.

The compounds (7) of the present invention also include those containing two or more asymmetric carbon atoms. They can exist as different stereoisomers (cis-form, trans-form). These stereoisomers and mixtures thereof are also included in the present invention.

A more detailed description will next be made of each step of the production process according to the present invention.

Step-1:

The N-benzylthiadiazoline derivative (3) or acid salt thereof is prepared by reacting the aminothiadiazole derivative represented by the formula (1) with the halogenotoluene derivative represented by the formula (2). The compound (3b) having a hydrogen atom as $R^2$ can be obtained by deacylation of the compound (3a) having as $R^2$ an acyl group. These N-benzylthiadiazoline derivatives (3a), (3b) and acid salts thereof are novel compounds.

Here, the examples of the acid salt of the N-benzylthiadiazoline derivative (3) include halogenated hydroacid salts, alkylsulfonates and arylsulfonates.

The above condensation reaction is preferably carried out in the presence of a base when the aminothiadiazole derivative (1) (amino-protected derivative) having an acyl group as $R^2$ is employed and by this reaction, the compound (3a) in the free form can be obtained. When the amino-thiadiazole derivative (1) (amino-unprotected derivative) having a hydrogen atom as $R^2$ is employed, the reaction is preferably effected in the absence of a base and by this reaction, an acid salt of the compound (3b) can be obtained. Examples of the base usable in the former case include sodium hydride, lithium hydride, potassium carbonate, sodium carbonate, sodium alcoholate, t-butoxy-potassium, sodium hydroxide, potassium hydroxide, triethylamine and diisopropylethylamine. Any solvent can be used here as long as it does not affect the reaction. Examples of the usable solvents include aprotic polar solvents such as N,N-dimethylformamide, dimethylsulfoxide and acetonitrile; ethers such as diethyl ether, tetrahydrofuran, dioxane, monoglyme and diglyme; halogenated hydrocarbons such as methylene chloride, chloroform and carbon tetrachloride; alcohols such as methanol, ethanol and propanol; and water. They may be used as needed either singly or in combination.

As a reaction accelerator, a phase transfer catalyst can be added. Examples of the phase transfer catalyst include quaternary ammonium salts such as tetramethylammonium chloride, tetraoctylammonium chloride and tetrabutylammonium bromide; pyridinium salts such as N-neopentyl-4-(N',N'-dimethylamino)pyridinium chloride and N-(2-ethylhexyl)-4-(N',N'-dimethylamino)pyridinium chloride; and quaternary phosphonium salts such as tetrabutylphosphonium bromide and tetraphenylphosphonium bromide.

The reaction temperature is generally −30° C. to 150° C., preferably 10° C. to 100° C. when an amino-protected derivative is used as the compound (1), while it is 20° C. to 200° C. when amino-unprotected derivative is used. The reaction time is generally 10 min. to 24 hours, preferably 1–10 hours when an amino-protected derivative is used, while it is 1–50 hours when an amino-unprotected derivative is used.

Particularly preferred examples of the production process according to the present reaction include the process in which the compound (3a) is obtained by preparing a metal salt of the aminothiadiazole derivative (1) (amino-protected derivative) having as $R^2$ an acyl group in an aprotic polar solvent such as N,N-dimethylformamide by using potassium carbonate as a base and then reacting the resulting metal salt with the halogenotoluene derivative (2) at a temperature of 0° C. to room temperature; and the process in which an acid salt of the compound (3b) is obtained by reacting, in the absence of a base, an aminothiadiazole derivative (1) (an amino-unprotected derivative) having as $R^2$ a hydrogen atom with a halogenotoluene derivative (2) at 50–100° C.

The deacylation reaction of the compound (3a) can be effected under the ordinary hydrolysis conditions, for example, in an aqueous alkaline solution such as an aqueous sodium hydroxide solution, aqueous potassium hydroxide solution or aqueous sodium carbonate solution or in an acidic solution such as hydrochloric acid or acetic acid at a temperature of room temperature to 100° C. in a solvent miscible with water such as ethanol, methanol, tetrahydrofuran or N,N-dimethylformamide or in a solventless manner.

Step-2:

The compound (5a) or (5b) is prepared by reacting the N-benzylthiadiazoline derivative (3a) or (3b), which has been obtained by the step-1 or the step-1 and the subsequent deacylation reaction, with the compound (4). Here, in the step-1, when the N-benzylthiadiazoline derivative (3) has been obtained in the form of an acid addition salt, it may be used as is for the above reaction or after converted into a free compound by using sodium hydroxide or the like.

As the above reaction, a cross-coupling reaction using a transfer metal catalyst is preferred. More specifically, in the case where Z in the formula (4) represents copper, lithium or a halogenated metal, it is preferred to conduct the reaction in the presence of a nickel complex, platinum complex or preferably palladium complex in an inert solvent such as benzene, toluene, ethyl ether, tetrahydrofuran, dioxane, acetonitrile or N,N-dimethylformamide. In the case where Z represents —B(OR$^4$)$_2$, on the other hand, it is preferred to carry out the reaction in the presence a nickel complex, platinum complex or preferably palladium complex in a suitable solvent such as benzene, toluene, ethyl ether, tetrahydrofuran, dioxane, acetonitrile, N,N-dimethylformamide, ethanol, methanol, propanol, dimethoxyethane or water under the basic conditions which have been prepared by the addition of an un-nucleophilic tertiary amine such as triethylamine or diisopropylamine, an inorganic base such as potassium carbonate, sodium carbonate, cesium carbonate, thallium carbonate, potassium hydroxide, sodium hydroxide or thallium hydroxide, or an alkoxide of such an alkali metal. When an inorganic base insoluble in an organic solvent is employed, the use of it in the form of an aqueous solution is required and it is preferred to conduct the reaction in the presence of a phase transfer catalyst such as tetra-n-butylammonium bromide or crown ether.

Examples of the palladium complex usable in the present reaction include tetrakis(triphenylphosphine)palladium, bis(dibenzylideneacetone)palladium, tris(dibenzylideneacetone)palladium and divalent palladium phosphine complexes.

Examples of the divalent palladium phosphine complex include bis(triphenylphosphine)palladium chloride, bis(triphenylphosphine)palladium bromide, bis(triphenylphosphine) palladium acetate, bis(triisopropylphosphite)palladium chloride, bis(triisopropylphosphite)palladium bromide, bis(triisopropylphosphite)palladium acetate, [1,2-bis(diphenylphosphino)ethane]palladium chloride, [1,2-bis(diphenylphosphino)ethane]palladium bromide, [1,2-bis(diphenylphosphino)ethane]palladium acetate, [1,3-bis(diphenylphosphino)propane]palladium chloride, [1,3-bis(diphenylphosphino)propane]palladium bromide, [1,3-bis(diphenylphosphino)propane]palladium acetate, [1,4-bis(diphenylphosphino)butane]palladium chloride, [1,4-bis(diphenylphsophino)butane]palladium bromide and [1,4-bis(diphenylphosphino)butane]palladium acetate.

The above reaction can also be carried out by activating the catalyst in the reaction mixture. Described specifically, tris(dibenzylideneacetone)dipalladium is added to the reaction mixture to which triphenylphosphine has been added and the resulting activated triphenylphosphine palladium complex is employed as the catalyst. It is also possible to carry out the activation of the catalyst by reacting a divalent palladium salt such as palladium chloride, palladium bromide or palladium acetate with a triarylphosphine, generally triphenylphosphine, in the presence of a reducing agent such as dialkylzinc, alkylzinc halide, dialkylmagnesium, alkylmagnesium halide, trialkylaluminum, dialkylaluminum halide, sodium borohydride, hydrazine or arylboric acid, preferably diethylzinc.

The present reaction is generally conducted at a temperature of room temperature to 150° C., preferably 60–100° C. and the reaction time generally ranges from 1 to 30 hours.

Incidentally, the compound represented by the formula (4) used in the present reaction is prepared by the following method.

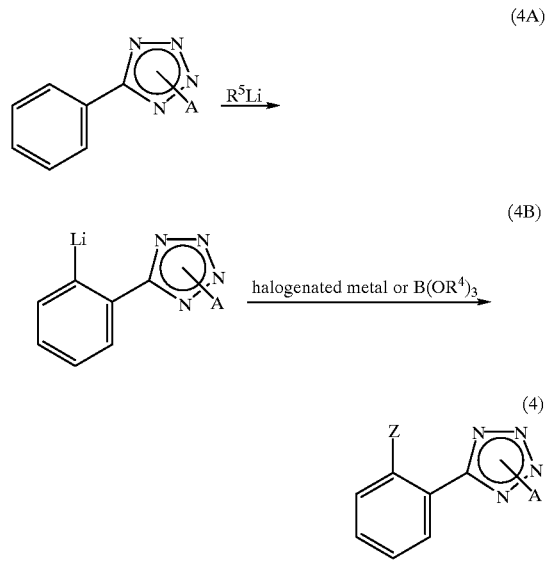

wherein $R^5$ represents a lower alkyl group, and A, $R^4$ and Z have the same meanings as defined above.

Described specifically, the compound (4) can be obtained by reacting a phenyltetrazole (4A) with alkyl lithium, preferably n-butyl lithium, to obtain it in the form of an alkali metal salt (4B) and then, reacting the salt with a halogenated metal or trialkyl borate.

By the reaction of the compound (3a) with the compound (4), the compound (5a) can be prepared and it can be converted into the compound (5b) by the elimination of the acyl group by deacylation. The deacylation can be carried out as in the deacylation of the above-described compound (3a).

Step-3:

The compound represented by the formula (5a) or an acid salt thereof is reacted with a 1-cyclopentene-1,2-dicarboxylic anhydride (6), whereby an N-biphenylmethylthiadiazoline derivative (7) is obtained.

The above reaction can be effected in solvents such as a halogenated hydrocarbon, e.g., methylene chloride, chloroform, carbon tetrachloride or chlorobenzene, an aromatic hydrocarbon, e.g., benzene or toluene, an ether, e.g., tetrahydrofuran or dioxane or an aprotic polar solvent, e.g., acetonitrile or N,N-dimethylformamide at a temperature of 0° C. to room temperature in the presence or absence of a base such as pyridine, picoline, N,N-dimethylaniline, N-methylmorpholine, dimethylamine, triethylamine, sodium carbonate or potassium carbonate at 70° C. to 100° C.

When A represents a tetrazolyl protective group, it can be eliminated as needed in an optional stage during the deacylation of the compound (5a) or the step-3. It is preferred to conduct the deprotection reaction in a water-containing alcohol containing hydrochloric acid, acetic acid or the like, or an ether such as dioxane or tetrahydrofuran at room temperature for 1–10 hours.

Step-a:

The N-benzylthiadiazoline derivative (3b) is reacted with 1-cyclopentene-1,2-dicarboxylic anhydride (6), whereby the compound (8) is obtained. Incidentally, the compound (8) is a novel compound.

This reaction can be conducted under the conditions similar to those for the above-described step-3.

Step-b:

The N-biphenylmethylthiadiazoline derivative (7) can be obtained by reacting the compound (8) with the compound (4) and then eliminating the tetrazolyl protective group as needed.

This reaction can be conducted under the conditions similar to those for the above-described step-2. When the product contains a tetrazolyl protective group, the tetrazolyl protective group can be eliminated in a similar manner to the above.

To obtain a salt of the N-biphenylmethylthiadiazoline derivative (7), for example, a potassium salt, it is only necessary to dissolve the compound (7) in a potassium hydroxide solution and then to precipitate its salt. It is preferred that the potassium hydroxide solution used here is a solution obtained by dissolving at least an equivalent amount, relative to the compound (7), of potassium hydroxide in water, methanol, ethanol, n-propyl alcohol, isopropyl alcohol, acetone or the like.

The isolation of the so-obtained N-biphenylmethylthiadiazoline derivative (7), salt thereof or an intermediate (3) for producing it can be conducted in a manner known per se in the art such as recrystallization or chromatography.

EXAMPLES

The present invention will hereinafter be described more specifically by the examples and referential examples. It should however be borne in mind that the present invention will not be limited to or by the following examples.

Referential Example 1 Synthesis of 2-amino-5-ethyl-1,3,4-thiadiazole

To a mixture of thiosemicarbazide (1.0 kg) and propionic acid (0.9 kg) was added dropwise concentrated sulfuric acid (2.0 liter) on ice, followed by stirring at 100° C. for 4 hours. After cooling, the reaction mixture was poured into ice water (10 liter) and the resulting mixture was made alkaline with 28% aqueous ammonia. Powders so precipitated were collected by filtration, washed successively with water, acetone and diethyl ether and then dried, whereby 1.2 kg of the title compound was obtained.

$^1$H-NMR (DMSO-d$_6$): 1.21(3H,t,J=8 Hz), 2.80(2H,q,J=8 Hz), 6.99(2H,br)

Referential Example 2 Synthesis of 5-ethyl-2-trifluoroacetylamino-1,3,4-thiadiazole To a suspension of 2-amino-5-ethyl-1,3,4-thiadiazole (1.29 g) in toluene (24 ml) was added triethylamine (3.1 ml) at room temperature, followed by the dropwise addition of trifluoroacetic anhydride (4.62 g) on ice. The resulting mixture was stirred at room temperature for one hour. Water and ethyl acetate were added to the reaction mixture to cause separation and the organic layer was dried over anhydrous magnesium sulfate, followed by removal through distillation. The crystals so obtained were dispersed in diisopropyl ether, collected by filtration and then dried, whereby 1.21 g of the title compound was obtained.

$^1$H-NMR (CDCl$_3$): 1.44(3H,t,J=8 Hz), 3.09(2H,q,J=8 Hz)

Referential Example 3 Synthesis of 4-bromobenzyl bromide

To a suspension of 4-bromotoluene (60 g) and N-bromosuccinimide (69 g) in carbon tetrachloride (300 ml) was added 2,2'-azobis(isobutylonitrile) (0.1 g). The resulting mixture was heated under reflux for 2 hours. After the reaction mixture was cooled, succinimide so precipitated was removed by filtration, and the filtrate was washed with saturated aqueous sodium hydrogencarbonate. The organic layer was dried over anhydrous magnesium sulfate, followed by removal through distillation. The oily substance so obtained was crystallized from n-hexane, whereby 52 g of the title compound was obtained.

$^1$H-NMR (CDCl$_3$): 4.43(2H,s), 7.26(2H,d,J=9 Hz), 7.47 (2H,d,J=9 Hz)

Referential Example 4 Synthesis of 4-iodobenzyl bromide

To a supension of 4-iodotoluene (50 g) and N-bromosuccininimide (45 g) in carbon tetrachloride (200 ml) was added 2,2'-azobis(isobutylonitrile) (0.1 g), followed by heating under reflux overnight. After the reaction mixture was cooled, succinimide so precipitated was filtered off and the filtrate was washed with saturated aqueous solution of sodium hydrogencarbonate. The organic layer was then dried over anhydrous magnesium sulfate, followed by removal through distillation, and the oily substance so obtained was crystallized from n-hexane, whereby 43 g of the title compound was obtained.

$^1$H-NMR (CDCl$_3$): 4.42(2H,s), 7.13(2H,d,J=9 Hz), 7.67 (2H,d,J=9 Hz)

Referential Example 5

Synthesis of 5-phenyl-1-triphenylmethyl-1H-tetrazole

To a solution of 5-phenyl-1H-tetrazole (21.9 g) and chlorotriphenylmethane (46 g) in methylene chloride (500 ml)

was added triethylamine (16.7 g). The resulting mixture was stirred at room temperature for one hour. The reaction mixture was washed successively with water, 10% aqueous citric acid solution and water and was then dried over anhydrous magnesium sulfate, followed by removal through distillation. The residue so obtained was dispersed in acetone, collected by filtration and then dried, whereby 51.8 g of the title compound was obtained.

$^1$H-NMR (CDCl$_3$): 7.15–7.38(15H,m), 7.44–7.48(3H,m), 8.13–8.16(2H,m)

Referential Example 6 Synthesis of 2-(1'-triphenylmethyl-1'H-tetrazol-5'-yl)phenylboric acid To a solution of 5-phenyl-1H-tetrazole (5.8 g) in tetrahydrofuran (45 ml) was added n-butyl lithium (1.6M hexane solution, 9.8 ml)) keeping the temperature below −20° C. under a nitrogen atmosphere, followed by stirring at −5° C. for one hour. After the addition of triisopropyl borate (6 ml) keeping the temperature below −20° C., the temperature was allowed to rise back to room temperature and the solvent was removed by distillation. To the residue so obtained, 3% aqueous acetic acid solution (40 ml) was added, followed by the reaction at room temperature for one hour. The powder so precipitated was collected by filtration and dried, whereby 7.0 g of the title compound was obtained.

$^1$H-NMR (CDCl$_3$): 1.83–1.87(4H,m), 3.72–3.77(4H,m), 7.15–7.53(17H,m), 8.14–8.25(2H,m).

Referential Example 7 Synthesis of 2-(1'-tert-butyl-1'H-tetrazol-5'-yl)phenylboric acid To a solution of 5-(2-bromophenyl)-1-tert-butyl-1H-tetrazole (5.6 g) in tetrahydrofuran (60 ml) was added n-butyl lithium (1.6M hexane solution) (15 ml) at 0–5° C. The resulting mixture was stirred at the same temperature for one hour. To the reaction mixture, triisopropyl borate (9.2 ml) was added, and the reaction mixture was stirred at room temperature for one hour. To the reaction mixture, 2N hydrochloric acid (50 ml) was added, and the reaction mixture was stirred for 30 minutes. Diethyl ether (100 ml) was added to cause separation, and the organic layer was dried over anhydrous magnesium sulfate, followed by removal through distillation. The oily substance so obtained was separated by column chromatography on silica gel, followed by crystallization from water, whereby 3.1 g of the title compound was obtained.

$^1$H-NMR (DMSO-d$_6$): 1.83(9H,s), 7.48–7.60(2H,m), 7.96(2H,br), 8.19–8.28(2H,m).

Referential Example 8 Synthesis of 2-(1'H-tetrazol-5'-yl)phenylboric acid

To a solution of 5-phenyl-1H-tetrazole (43.8 g) in tetrahydrofuran (750 ml) was added n-butyl lithium (1.6M hexane solution) (450 ml) keeping the temperature below 10° C. The resulting mixture was stirred at 5° C. for two hours. To the reaction mixture, triisopropyl borate (150 ml) was added, and the reaction mixture was stirred at room temperature overnight. After 2N hydrochloric acid (500 ml) was added to the reaction mixture, they were stirred for 30 minutes to cause separation. The aqueous layer was extracted further with diethyl ether (500 ml). The organic layers were combined, followed by extraction three times with 1N potassium hydroxide (300 ml). The aqueous layers were made acidic with 12N hydrochloric acid and then allowed to stand overnight. The crystals so precipitated were collected by filtration and dried, whereby 51.2 g of the title compound was obtained.

$^1$H-NMR (DMSO-d$_6$): 7.49–7.54(2H,m), 7.56–7.64(1H, m), 7.65–7.73(1H,m)

EXAMPLE 1

Synthesis of 5-ethyl-2-trifluoroacetylimino-3-(4-bromobenzyl)-1,3,4-thiadiazoline To a suspension of sodium hydride (4.4 g) in N,N-dimethylformamide (100 ml) was added 5-ethyl-2-trifluoroacetylamino-1,3,4-thiadiazole (24 g) in three portions on ice. After stirring at the same temperature for 30 minutes, to the resulting mixture was added 4-bromobenzyl bromide (25 g), followed by stirring at room temperature for one hour. To the reaction mixture, ethyl acetate (500 ml) was added. The resulting mixture was washed successively with 10% aqueous citric acid solution and water and was dried over anhydrous magnesium sulfate, followed by removal through distillation. The residue so obtained was dispersed in a 2:3 mixed solvent of diisopropyl ether and n-hexane, collected by filtration and then dried, whereby 24.8 g of the title compound was obtained.

Melting point: 82–83° C. $^1$H-NMR (CDCl$_3$)δ: 1.36(3H, t,J=8 Hz), 2.92(2H,q,J=8 Hz), 5.48(2H,s), 7.35(2H,d,J=8 Hz), 7.49(2H,d,J=8 Hz).

EXAMPLE 2

Synthesis of 5-ethyl-2-trifluoroacetylimino-3-(4-iodobenzyl)-1,3,4-thiadiazoline (1) To a suspension of sodium hydride (0.44 g) in N,N-dimethylformamide (10 ml) was added 5-ethyl-2-trifluoroacetylamino-1,3,4-thiadiazole (2.25 g) in three portions on ice. After the resulting mixture was stirred at the same temperature for 30 minutes, to the mixture was added 4-iodobenzyl bromide (2.97 g), and the mixture was stirred at room temperature for two hours. To the reaction mixture, ethyl acetate (50 ml) was added. The resulting mixture was washed successively with 10% aqueous citric acid solution and water and dried over anhydrous magnesium sulfate, followed by the removal through distillation. The residue so obtained was crystallized from n-hexane, collected by filtration and then dried, whereby 2.2 g of the title compound was obtained.

Melting point: 92–93° C. $^1$H-NMR (CDCl$_3$): 1.36(3H,t, J=7 Hz), 2.91(2H,q,J=7 Hz), 5.46(2H,s), 7.22(2H,d,J=8 Hz), 7.70(2H,d,J=8 Hz).

(2) To a solution of 5-ethyl-2-trifluoroacetylamino-1,3,4-thiadiazole (22.5 g) and 4-iodobenzyl bromide (32.7 g) in N,N-dimethylformamide (100 ml) was added potassium carbonate (13.8 g), followed by stirring at room temperature overnight. To the reaction mixture, ethyl acetate (500 ml) was added. The resulting mixture was washed three times with 10% aqueous citric acid solution, followed by drying over anhydrous magnesium sulfate. The solvent was then distilled off. The oily substance so obtained was separated by column chromatography on silica gel. The crystals so obtained were dispersed in n-hexane, collected by filtration and then dried, whereby 33.9 g of the title compound was obtained.

EXAMPLE 3

Synthesis of 5-ethyl-2-imino-3-(4-iodobenzyl)-1,3,4-thiadiazoline hydrobromide (1) A solution of 2-amino-5-ethyl-1,3,4-thiadiazole (42.6 g) and 4-iodobenzyl bromide (89.1 g) in ethanol (500 ml)

was heated under reflux for 20 hours. After the reaction mixture was cooled, the crystals so precipitated were collected by filtration and then dried, whereby 83 g of the title compound was obtained.

Melting point: 257–259° C. $^1$H-NMR (DMSO-d$_6$): 1.21 (3H,t,J=8 Hz), 2.89(2H,q,J=8 Hz), 5.38(2H,s), 7.17(2H,d, J=8 Hz), 7.78(2H,d,J=8 Hz).

(2) A solution of 2-amino-5-ethyl-1,3,4-thiadiazole (645 mg) and 4-iodobenzyl bromide (1.49 g) in methanol (5 ml) was heated under reflux for 2 hours. After the reaction mixture was cooled, the crystals so precipitated were collected by filtration and then dried, whereby 1.12 g of the title compound was obtained.

(3) To isopropyl alcohol (10 ml) was added 2-amino-5-ethyl-1,3,4-thiadiazole (645 mg) and 4-iodobenzyl bromide (1.49 g), followed by heating under reflux for 2 hours. After the reaction mixture was cooled, the crystals so precipitated were collected by filtration and dried, whereby 1.33 g of the title compound was obtained.

(4) To acetone (10 ml) was added 2-amino-5-ethyl-1,3,4-thiadiazole (645 mg) and 4-iodobenzyl bromide (1.49 g), followed by heating under reflux for 3 hours. After the reaction mixture was cooled, the crystals so precipitated were collected by filtration and dried, whereby 1.09 g of the title compound was obtained.

(5) To acetonitrile (10 ml) was added 2-amino-5-ethyl-1, 3,4-thiadiazole (645 mg) and 4-iodobenzyl bromide (1.49 g), followed by heating under reflux for 20 hours. After the reaction mixture was cooled, the crystals so precipitated were collected by filtration and dried, whereby 1.52 g of the title compound was obtained.

EXAMPLE 4

Synthesis of 5-ethyl-2-imino-3-(4-iodobenzyl)-1,3,4-thiadiazoline

To a solution of 5-ethyl-3-(4-iodobenzyl)-2-trifluoroacetylimino-1,3,4-thiadiazoline (44.1 g) in tetrahydrofuran (300 ml) was added 2N sodium hydroxide (100 ml), followed by stirring at room temperature overnight. Water (300 ml) was added to the reaction mixture, followed by extraction with chloroform (250 ml) twice. The organic layers were washed with a saturated aqueous sodium hydrogencarbonate and were dried over anhydrous magnesium sulfate, followed by removal through distillation. The oily substance so obtained was crystallized from diisopropyl ether, whereby 32.3 g of the title compound was obtained.

Melting point: 102–104° C. $^1$H-NMR (CDCl$_3$): 1.21(3H, t,J=7 Hz), 2.60(2H,q,J=7 Hz), 4.98(2H,s), 7.11(2H,d,J=8 Hz), 7.66(2H,d,J=8 Hz).

EXAMPLE 5

Synthesis of 5-ethyl-2-imino-3-(4-iodobenzyl)-1,3,4-thiadiazoline

In chloroform (50 ml), 5-ethyl-2-imino-3-(4-iodobenzyl)-1,3,4-thiadiazoline hydrobromide (2.89 g) was suspended. To the resulting suspension was added 0.5N sodium hydroxide (25 ml), and they were stirred for 30 minutes. After separation, the organic layer was dried over anhydrous magnesium sulfate. The oily substance so obtained was crystallized from diisopropyl ether, whereby 1.85 g of the title compound was obtained.

The resulting compound was similar to the compound obtained in Example 4.

EXAMPLE 6

Synthesis of 5-ethyl-2-trifluoroacetylimino-3-[2'-(1-triphenylmethyl-1H-tetrazol-5-yl)biphenyl-4-yl]methyl-1,3,4-thiadiazoline (1) To a mixed solvent of toluene (7 ml) and water (2 ml) was added 2-(1'-triphenylmethyl-1'H-tetrazol-5'-yl) phenylboric acid-tetrahydrofuran complex (900 mg), 5-ethyl-3-(4-bromobenzyl)-2-trifluoroacetylimino-1,3,4-thiadiazoline (870 mg) and sodium carbonate (424 mg). To the resulting solution, tetrakis(triphenylphosphine)-palladium (70 mg) was added, followed by heating under reflux for 6 hours. Ethyl acetate (20 ml) and water (20 ml) were added to the reaction mixture to cause separation and the organic layer was dried over anhydrous magnesium sulfate, followed by the removal through distillation. The residue so obtained was separated by column chromatography on silica gel, whereby 70 mg of the title compound was obtained.

Melting point: 167–170° C. $^1$H-NMR (CDCl$_3$): 1.30(3H, t,J=7 Hz), 2.84(2H,q,J=7 Hz), 5.41(2H,s), 6.88–7.36(20H, m), 7.45–7.50(2H,m), 7.93–7.97(1H,m).

(2) To a solution of 5-phenyl-1-triphenylmethyl-1H-tetrazole (1.2 g) in tetrahydrofuran (10 ml) was added dropwise n-butyl lithium (1.6M hexane solution, 2.5 ml) keeping the temperature below −20° C., followed by stirring at −5° C. for one hour. After zinc chloride (1.0M diethyl ether solution, 3.5 ml) was added dropwise to the reaction mixture keeping the temperature below −30° C., they were stirred at room temperature for 2 hours. To the reaction mixture were added 3-(4-bromobenzyl)-5-ethyl-2-trifluoroacetylimino- 1,3,4-thiadiazoline (1.0 g) and tetrakis (triphenylphosphine)palladium (50 mg) were added, followed by heating under reflux overnight. After ethyl acetate (50 ml) was added to the reaction mixture, the resulting mixture was washed with 10% aqueous citric acid solution and was dried over anhydrous magnesium sulfate, followed by removal through distillation. The residue so obtained was separated by column chromatography on silica gel, whereby 205 mg of the title compound was obtained.

(3) To a solution of 5-phenyl-1-triphenylmethyl-1H-tetrazole (2.3 g) in tetrahydrofuran (20 ml) was added dropwise n-butyl lithium (1.6M hexane solution, 4.0 ml) keeping the temperature below −20° C., followed by stirring at −5° C. for one hour. Zinc chloride (1.0M diethyl ether solution, 7.0 ml) was added dropwise keeping the temperature below −30° C., followed by stirring at room temperature for two hours. To the reaction mixture, 3-(4-iodobenzyl)-5-ethyl-2-trifluoroacetylimino-1,3,4-thiadiazoline (1.4 g) and tetrakis(triphenylphosphine)-palladium (100 mg) were added, followed by heating under reflux overnight. After ethyl acetate (50 ml) was added to the reaction mixture, the resulting mixture was washed with 10% aqueous citric acid solution and dried over anhydrous magnesium sulfate, followed by removal through distillation. The residue so obtained was separated by column chromatography on silica gel, whereby 830 mg of the title compound was obtained.

(4) To a solution of 5-phenyl-1-triphenylmethyl-1H-tetrazole (1.0 g) in tetrahydrofuran (10 ml) was added n-butyl lithium (1.6M hexane solution, 2.0 ml) on ice, followed by stirring at the same temperature for one hour. Magnesium bromide (0.5M tetrahydrofuran solution, 6.0 ml) was added to the resulting solution, followed by stirring at room temperature for 30 minutes. To the reaction mixture were added 3-(4-iodobenzyl)-5-ethyl-2-trifluoroacetylimino-1,3,4-thiadiazoline (880 mg) and tetrakis (triphenylphosphine)palladium (120 mg), followed by heating under reflux for 2 hours. Ethyl acetate (50 ml) was added to the reaction mixture, and the resulting mixture was washed with 10% aqueous citric acid solution and dried over anhydrous magnesium sulfate, followed by removal through distillation. The residue so obtained was separated by column chromatography on silica gel, whereby 120 mg of the title compound was obtained.

EXAMPLE 7

Synthesis of 3-[2'-(1-tert-butyl-1H-tetrazol-5-yl) biphenyl-4-yl]methyl-5-ethyl-2-trifluoroacetylimino-1,3,4-thiadiazoline To a solution of 5-phenyl-1-tert-butyl-1H-tetrazole (1.0 g) in tetrahydrofuran (20 ml) was added dropwise n-butyl lithium (1.6M hexane solution, 3.5 ml) keeping the temperature below −20° C., followed by stirring at −5° C. for one hour. Zinc chloride (1.0M diethyl ether solution, 6.0 ml) was added dropwise to the reaction mixture keeping the temperature below −30° C., followed by stirring at room temperature for 2 hours. To the resulting mixture were added 5-ethyl-3-(4-iodobenzyl)-2-trifluoroacetylimino-1,3,4-thiadiazoline (1.2 g) and tetrakis(triphenyl-phosphine)palladium (100 mg), and they were heated under reflux overnight. Ethyl acetate (100 ml) was added to the reaction mixture, and the resulting mixture was washed with 10% aqueous citric acid solution and dried over anhydrous magnesium sulfate, followed by removal through distillation. The residue so obtained was separated by column chromatography on silica gel, whereby 830 mg of the title compound was obtained in the oily form.

$^1$H-NMR (CDCl$_3$): 1.38(3H,t,J=7 Hz), 1.49(9H,s), 2.93 (2H,q,J=7 Hz), 5.53(2H,s), 7.17(2H,d,J=8 Hz), 7.38(2H,d, J=8 Hz), 7.32–7.55(3H,m), 7.90–7.93(1H,m).

EXAMPLE 8

Synthesis of 5-ethyl-2-imino-3-[2'-(1H-tetrazol-5-yl) biphenyl-4-yl]methyl-1,3,4-thiadiazoline hydrochloride To a solution of 5-ethyl-2-trifluoroacetylimino-3-[2'-(1-triphenylmethyl-1H-tetrazol-5-yl)biphenyl-4-yl]methyl-1,3,4-thiadiazoline (700 mg) in 1,4-dioxane (10 ml) was added 12N hydrochloric acid (2ml), and they were stirred at room temperature for 18 hours. The solvent was distilled off from the reaction mixture. The residue so obtained was dispersed in water, collected by filtration and then dried, whereby 250 mg of the title compound was obtained.

Melting point: 205–206° C. $^1$H-NMR (DMSO-d$_6$): 1.22 (3H,t,J=8 Hz), 2.89(2H,q,J=8 Hz), 5.43(2H,s), 7.14(2H,d, J=8 Hz), 7.28(2H,d,J=8 Hz), 7.53–7.73(4H,m)

EXAMPLE 9

Synthesis of 5-ethyl-2-imino-3-[2'-(1H-tetrazol-5-yl) biphenyl-4-yl]methyl-1,3,4-thiadiazoline hydrochloride To a mixed solvent of toluene (4 ml) and water (1 ml) were added 2-(1'-triphenylmethyl-1'H-tetrazol-5'-yl)phenyl-boric acid—tetrahydrofuran complex (650 mg), 5-ethyl-2-imino-3-(4-iodobenzyl)-1,3,4-thiazoline (345 mg) and sodium carbonate (230 mg). To the resulting solution was added bis(triphenylphosphine)palladium chloride (35 mg), and they were heated under reflux for 6 hours. Chloroform (100 ml) was added to the reaction mixture to cause separation, and the organic layer was dried over anhydrous magnesium sulfate, followed by removal through distillation, whereby a crude product of 5-ethyl-2-imino-3-[2'-(1-triphenyl-methyl-1H-tetrazol-5-yl)biphenyl-4-yl] methyl-1,3,4-thiadiazoline was obtained.

$^1$H-NMR (CDCl$_3$): 1.19(3H,t,J=7 Hz), 2.57(2H,q,J=7 Hz), 4.96(2H,s), 6.89–6.93(6H,m), 7.08–7.51(16H,m), 7.90–7.92(1H,m).

The crude product was dissolved in 1,4-dioxane (10 ml). To the resulting solution was added 12N hydrochloric acid (2 ml), followed by stirring at room temperature overnight. The solvent was distilled off. To the residue were added ethyl acetate (50 ml) and 1N sodium hydroxide (50 ml) to cause separation. The aqueous layer was made acidic with 12N hydrochloric acid. Powders so precipitated were collected by filtration and dried, whereby 40 mg of the title compound was obtained.

The compound so obtained was similar to the compound obtained in Example 8.

EXAMPLE 10

Synthesis of 5-ethyl-2-imino-3-[2'-(1H-tetrazol-5-yl) biphenyl-4-yl]methyl-1,3,4-thiadiazoline (1) To methanol (100 ml) were added 5-ethyl-2-imino-3-(4-iodobenzyl)-1,3,4-thiadiazoline (6.9 g), 2-(1'H-tetrazole-5'-yl)phenylboric acid (5.7 g) and bis(triphenylphosphine) palladium chloride (0.7 g). To the resulting mixture was added 2N sodium hydroxide (30 ml), and they were heated under reflux for 90 minutes. Ethyl acetate (200 ml) and 2N sodium hydroxide (200 ml) were added to the reaction mixture to cause separation. The aqueous layer was neutralized with 12N hydrochloric acid and powders so precipitated were collected by filtration. The powders were washed successively with water, ethanol and diethyl ether and then dried, whereby 6.1 g of the title compound was obtained.

Melting point: 148–149° C. $^1$H-NMR (DMSO-d$_6$): 1.15 (3H,t,J=7 Hz), 2.70(2H,q,J=7 Hz), 5.10(2H,s), 7.09(2H,d, J=8 Hz), 7.18(2H,d,J=8 Hz), 7.44–7.63(4H,m).

(2) To methanol (10 ml) were added 5-ethyl-2-imino-3-(4-iodobenzyl)-1,3,4-thiadiazoline (690 mg), 2-(1H'-tetrazol-5'-yl)phenylboric acid (570 mg), palladium acetate (23 mg) and triphenylphosphine (53 mg). To the resulting mixture was added 2N sodium hdyroxide (3 ml), and they were heated under reflux for 90 minutes. To the reaction mixture, ethyl acetate (20 ml) and 2N sodium hydroxide (20 ml) were added to cause separation. The aqueous layer was neutralized with 12N hydrochloric acid. Powders so precipitated were collected by filtration. The powders were washed successively with water, ethanol and diethyl ether and then dried, whereby 490 mg of the title compound was obtained.

(3) To methanol (10 ml) were added 5-ethyl-2-imino-3-(4-iodobenzyl)-1,3,4-thiadiazoline (690 mg), 2-(1'H-tetrazol-5'-yl)phenylboric acid (570 mg), palladium chloride (18 mg) and triphenylphosphine (53 mg). To the resulting mixture was added 2N sodium hydroxide (3 ml) and they were stirred under reflux for 3 hours. To the reaction mixture, ethyl acetate (20 ml) and 2N sodium hydroxide (20 ml) were added to cause separation. The aqueous layer was neutralized with 12N hydrochloric acid and the powders so precipitated were collected by filtration. The powders were washed successively with water, ethanol and diethyl ether and then dried, whereby 610 mg of the title compound was obtained.

(4) To methanol (10 ml), 5-ethyl-2-imino-3-(4-iodobenzyl)-1,3,4-thiadiazoline (690 mg), 2-(1'H-tetrazol-5'-yl)phenylboric acid (570 mg) and tetrakis(triphenyl-phosphine)palladium (115 mg). To the resulting mixture was added 2N sodium hydroxide (3 ml) and they were heated under reflux for 5 hours. To the reaction mixture were added ethyl acetate (20 ml) and 2N sodium hydroxide (20 ml) to cause separation. The aqueous layer was neutralized with 12N hydrochloric acid, and the powders so precipitated were collected by filtration. The powders were washed successively with water, ethanol and diethyl ether and then dried, whereby 670 mg of the title compound was obtained.

EXAMPLE 11

Synthesis of 5-ethyl-2-imino-3-[2'-(1H-tetrazol-5-yl) biphenyl-4-yl]methyl-1,3,4-thiadiazoline (1) To methanol (10 ml) were added 5-ethyl-2-imino-3-(4-iodobenzyl)-1,3,4-thiadiazoline hydrobromic acid salt (850 mg), 2-(1'H-tetrazol-5'-yl)phenylboric acid (570 mg) and bis(triphenylphosphine)palladium chloride (70 mg) were added. To the resulting mixture was added 3N sodium hydroxide (3 ml), and they were heated under reflux for 2 hours. To the reaction mixture, ethyl acetate (20 ml) and 2N sodium hydroxide (20 ml) were added to cause separation. The aqueous layer was neutralized with 12N hydrochloric acid, and powders so precipitated were collected by filtration. The powders were washed successively with water, ethanol and diethyl ether and then dried, whereby 730 mg of the title compound was obtained.

The compound so obtained was the same as that obtained in Example 10.

(2) To methanol (750 ml) were added 5-ethyl-2-imino-3-(4-iodobenzyl)-1,3,4-thiadiazoline hydrobromide (63.9 g), 2-(1'H-tetrazol-5'-yl)phenylboric acid (42.8 g), palladium chloride (0.8 g) and triphenylphosphine (2.4 g). To the resulting mixture was added 3N sodium hydroxide (225 ml), and they were heated under reflux for 24 hours. To the reaction mixture were added ethyl acetate (2 liter) and 2N sodium hydroxide (1.5 liter) were added to cause separation. The aqueous layer was neutralized with 12N hydrochloric acid, and the powders so precipitated were collected by filtration. The powders were washed successively with water, ethanol and diethyl ether and then dried, whereby 48 g of the title compound was obtained.

(3) To methanol (10 ml) were added 5-ethyl-2-imino-3-(4-iodobenzyl)-1,3,4-thiadiazoline hydrobromic acid salt (852 mg), 2-(1'H-tetrazol-5'-yl)phenylboric acid (570 mg) and tetrakis(triphenylphosphine)palladium (116 mg). To the resulting mixture was added 3N sodium hydroxide (3 ml), and they were heated under reflux for two hours. To the reaction mixture were added ethyl acetate (20 ml) and 2N sodium hydroxide (20 ml) to cause separation. The aqueous layer was neutralized with 12N hydrochloric acid, and powders so precipitated were collected by filtration. The powders were washed successively with water, ethanol and diethyl ether and then dried, whereby 570 mg of the title compound was obtained.

(4) To methanol (10 ml) were added 5-ethyl-2-imino-3-(4-iodobenzyl)-1,3,4-thiadiazoline hydrobromide (850 mg), 2-(1'H-tetrazol-5'-yl)phenylboric acid (570 mg), triphenylphosphine (60 mg) and 10% palladium carbon (100 mg). To the resulting mixture was added 3N sodium hydroxide (3 ml), and they were heated under reflux for 17 hours under a nitrogen atmosphere. From the reaction mixture, 10% palladium carbon was removed by filtration, an d to the filtrate were added 0.5N sodium hydroxide (10 ml) and ethyl acetate (10 ml) to cause separation. The aqueous layer was neutralized with 12N hydrochloric acid, and the powders so precipitated were collected by filtration. The powders were washed successively with water, ethanol and diethyl ether and then dried, whereby 70 mg of the title compound was obtained.

EXAMPLE 12

Synthesis of 2-[[5-ethyl-3-(4-iodobenzyl)-1,3,4-thiadiazolin-2-yliden]aminocarbonyl]-1-cyclopentene-carboxylic acid To a solution of 5-ethyl-2-imino-3-(4-iodobenzyl)-1,3,4-thiadiazoline (17.3 g) in chloroform (200 ml) was added 1-cyclopentene-1,2-dicarboxylic anhydride (7.5 g), and they were stirred at room temperature for one hour. The reaction mixture was washed with 1N hydrochloric acid and dried over anhydrous magnesium sulfate, followed by removal through distillation. The residue so obtained was dispersed in diethyl ether and collected by filtration, whereby 23.8 g of the title compound was obtained.

Melting point: 188–190° C. $^1$H-NMR (DMSO-$d_6$): 1.38 (3H,t,J=7 Hz), 1.82–1.94(2H,m), 2.93(2H,q,J=7 Hz), 2.96–3.10(4H,m), 5.46(2H,s), 7.17(2H,d,J=8 Hz), 7.70(2H, d,J=8 Hz).

EXAMPLE 13

Synthesis of 2-[[5-ethyl-3-[2'-(1H-tetrazol-5-yl)-biphenyl-4-yl]methyl-1,3,4-thiadiazolin-2-yliden]-aminocarbonyl]-1-cyclopentenecarboxylic acid To a solution of 5-ethyl-2-imino-3-[[2'-(1H-tetrazol-5-yl) biphenyl-4-yl]methyl]-1,3,4-thiadiazoline hydrochloride (200 mg) in N,N-dimethylformamide (3 ml) was added 1-cyclopentene-1,2-dicarboxylic anhydride (100 mg), and they were stirred at room temperature for 3 days. To the reaction mixture was added water (20 ml), and powders so precipitated were collected by filtration. The powders were washed successively with water, ethanol and diethyl ether and then dried, whereby 160 mg of the title compound was obtained.

Melting point: 234–235° C. $^1$H-NMR (DMSO-$d_6$): 1.25 (3H,t,J=8 Hz), 1.83–1.94(2H,m), 2.71–2.88(4H,m), 2.92 (2H,q,J=8 Hz), 5.50(2H,s), 7.09(2H,d,J=8 Hz), 7.33(2H,d, J=8 Hz), 7.53–7.70(4H,m).

EXAMPLE 14

Synthesis of 2-[[5-ethyl-3-[2'-(1H-tetrazol-5-yl)-biphenyl-4-yl]methyl-1,3,4-thiadiazolin-2-yliden]-aminocarbonyl]-1-cyclopentenecarboxylic acid To a solution of 5-ethyl-2-imino-3-[[2'-(1H-tetrazol-5-yl) biphenyl-4-yl]methyl]-1,3,4-thiadiazoline (3.63 g) in N,N-dimethylformamide (30 ml) was added 1-cyclopentene-1,2-dicarboxylic anhydride (1.44 g), and they were stirred at room temperature for 6 hours. To the reaction mixture was added water (200 ml), and powders so precipitated were collected by filtration. The powders so obtained were washed successively with water and methanol and then dried, whereby 4.53 g of the title compound was obtained.

The compound so obtained was the same as the compound obtained in Example 13.

EXAMPLE 15

Synthesis of 2-[[5-ethyl-3-[2'-(1H-tetrazol-5-yl) biphenyl-4-yl]methyl-1,3,4-thiadiazolin-2-yliden] aminocarbonyl]-1-cylopentenecarboxylic acid (1) To a mixed solvent of toluene (8 ml) and water (2 ml) were added 2-[[5-ethyl-3-(4-iodobenzyl)-1,3,4-thiadiazolin-2-yliden]aminocarbonyl]-1-cyclopentenecarboxylic acid (483 mg), 2-(1'-triphenylmethyl-1'H-tetrazol-5'-yl) phenylboric acid-tetrahydrofuran complex (648 mg) and sodium carbonate (230 mg). To the resulting mixture were added bis(triphenylphosphine)palladium chloride (35 mg), and they were heated under reflux for 90 minutes. Chloroform (100 ml) was added to the reaction mixture to cause separation, and the organic layer was dried over anhydrous magnesium sulfate, followed by removal through distillation, whereby a crude product of 2-[[5-ethyl-3-[2'-(1-triphenylmethyl-1H-tetrazol-5-yl)biphenyl-4-yl]methyl-1,3, 4-thiadiazolin-2-yliden]aminocarbonyl]-1-cyclopentenecarboxylic acid was obtained.

$^1$H-NMR (CDCl$_3$): 1.33(3H,t,J=7 Hz), 1.83–1.89(2H,m), 2.86(2H,q,J=7 Hz), 2.96–3.11(4H,m), 5.43(2H,s), 6.88–6.92 (6H,m), 7.12–7.38(14H,m), 7.42–7.53(2H,m), 7.91–7.94 (1H,m).

The crude product so obtained was dissolved in 1,4-dioxane (10 ml). To the resulting solution was added 12N hydrochloric acid (2 ml), and they were stirred at room temperature overnight. The solvent was distilled off and to the residue were added ethyl acetate (20 ml) and 1N sodium hydroxide (20 ml) to cause separation. The aqueous layer was made acidic with 12N hydrochloric acid. The powders so precipitated were collected by filtration and dried, whereby 360 mg of the title compound was obtained.

The compound so obtained was same as the compound obtained in Example 13.

(2) To a mixed solvent of methanol (5 ml) and 2N sodium hydroxide (1 ml) were added 2-[[5-ethyl-3-(4-iodobenzyl)-1,3,4-thiadiazolin-2-yliden]aminocarbonyl]-1-cyclopentene-carboxylic acid (483 mg) and 2-(1'-tert-butyl-1'H-tetrazol-5'-yl)phenylboric acid (370 mg). To the resulting mixture was added bis(triphenylphosphine) palladium chloride (35 mg), and they were heated under reflux for 90 minutes. Chloroform (100 ml) was added to the reaction mixture to cause separation and the organic layer was dried over anhydrous magnesium sulfate, followed by removal through distillation. The residue so obtained was separated by column chromatography on silica gel, whereby 690 mg of 2-[[5-ethyl-3-[2'-(1-tert-butyl-1H-tetrazol-5-yl) biphenyl-4-yl]methyl-1,3,4-thiadiazolin-2-yliden] aminocarbonyl]-1-cylopentenecarboxylic acid was obtained as an oil.

$^1$H-NMR (CDCl$_3$): 1.40(3H,t,J=8 Hz), 1.50(9H,s), 1.85–1.91(2H,m), 2.94(2H,q,J=8 Hz), 2.90–3.15(4H,m), 5.52(2H,s), 7.17(2H,d,J=8 Hz), 7.35(2H,d,J=8 Hz), 7.39–7.53(3H,m), 7.90–7.93(1H,m).

The oily product so obtained was dissolved in 1,4-dioxane (5 ml). To the resulting solution was added 12N hydrochloric acid (5 ml), and they were heated under reflux overnight. To the reaction mixture were added ethyl acetate (30 ml) and 1N sodium hydroxide (20 ml) to cause separation. The aqueous layer was made acidic with 12N hydrochloric acid. The powders so precipitated were collected by filtration and then dried, whereby 70 mg of the title compound was obtained.

(3) To a mixed solvent of methanol (5 ml) and 2N sodium hydroxide (2 ml) were added 2-[[5-ethyl-3-(4-iodobenzyl)-1,3,4-thiadiazolin-2-yliden]aminocarbonyl]-1-cylopentenecarboxylic acid (483 mg) and 2-(1'H-tetrazol-5'-yl)phenyl-boric acid (285 mg). To the resulting mixture was added bis(triphenylphosphine)palladium chloride (35 mg), and they were heated under reflux for 6.5 hours. To the reaction mixture were added ethyl acetate (50 ml) and 2N sodium hydroxide (10 ml) to cause separation. The aqueous layer was made acidic with 12N hydrochloric acid. Powders so precipitated were collected by filtration and then dried, whereby 380 mg of the title compound were obtained.

EXAMPLE 16

Synthesis of 2-[[5-ethyl-3-[2'-(1H-tetrazol-5-yl) biphenyl-4-yl ]methyl-1,3,4-thiadiazolin-2-yliden] aminocarbonyl]-1-cyclopentenecarboxylic acid dipotassium salt To 2-[[5-ethyl-3-[2'-(1H-tetrazol-5-yl)biphenyl-4-yl] methyl-1,3,4-thiadiazolin-2-yliden]aminocarbonyl]-1-cyclopentenecarboxylic acid (10 g) were added 0.1N potassium hydroxide in ethanol solution (400 ml) and ethanol (600 ml) to dissolve the former in the latter. The resulting solution was concentrated to about 200 ml in total. The crystals so precipitated were collected by filtration, washed with ethanol and then dried, whereby 11 g of the title compound was obtained.

Melting point: 300° C. or higher IR(KBr)cm$^{-1}$: 1642 (—COOK), 1570 (=N—CO—) $^1$H-NMR (D$_2$O): 1.23(3H, t,J=8 Hz), 1.95–2.00(2H,m), 2.66–2.86(6H,m), 5.49(2H,s), 7.04(2H,d,J=8 Hz), 7.31(2H,d,J=8 Hz), 7.37–7.39(1H,m), 7.51–7.62(3H,m).

EXAMPLE 17

Synthesis of 2-[[5-ethyl-3-[2'-(1H-tetrazol-5-yl) biphenyl-4-yl]methyl-1,3,4-thiadiazolin-2-yliden] aminocarbonyl]-1-cyclopentenecarboxylic acid monopotassium salt To 2-[[5-ethyl-3-[2'-(1H-tetrazol-5-yl)biphenyl-4-yl] methyl-1,3,4-thiadiazolin-2-yliden]aminocarbonyl]-1-cyclopentenecarboxylic acid (206 mg) were added a 0.05N potassium hydroxide in ethanol solution (8.3 ml) and ethanol (50 ml) to dissolve the former in the latter. The solvent was then distilled off. To the residue was added ethanol. The solid so precipitated was collected by filtration and then dried, whereby 180 mg of the title compound was obtained. IR(KBr)cm$^{-1}$: 1680(—COOH), 1570(=N—CO—)

Capability of Exploitation in Industry

According to the present invention, N-biphenylmethylthiadiazoline derivatives (7) and salts thereof which are useful as pharmaceuticals can be prepared at a high yield and advantageously from the industrial viewpoint.

We claim:

1. An N-benzylthiadiazoline derivative represented by the following formula (3):

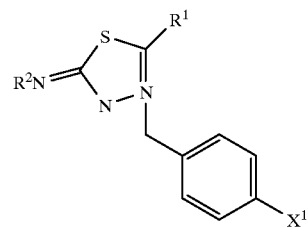

(3)

wherein R$^1$ represents a lower alkyl group, R$^2$ represents a hydrogen atom or an acyl group and X$^1$ represents a halogen atom, or an acid salt thereof, with the proviso that when R$^2$ contains a benzene ring, R$^2$ is lower aralkyloxycarbonyl.

2. A process for producing an N-benzylthiadiazoline derivative represented by the following formula (3):

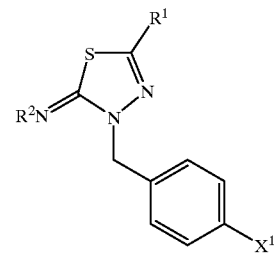

(3)

wherein R$^1$ represents a lower alkyl group, X$^1$ represents a halogen atom and R$^2$ represents a hydrogen atom or an acyl group or an acid salt thereof, which comprises reacting an aminothiazole derivative represented by the following formula (1):

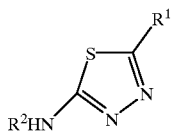
(1)

wherein $R^1$ and $R^2$ have the same meanings as defined above with a halogenotoluene derivative represented by the following formula (2):

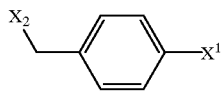
(2)

wherein $X_1$ has the same meaning as defined above, $X^2$ represents a halogen atom or $-SO_3R^3$ in which $R^3$ represents an alkyl or aryl group in the presence or absence of a base and then optionally eliminating an acyl group.

3. A process for producing the compound represented by the following formula (5):

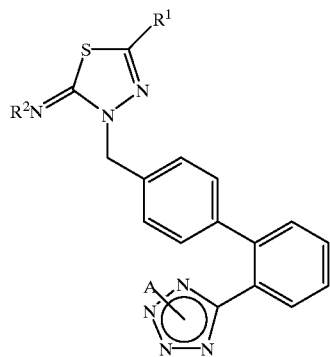
(5)

wherein $R^1$ represents a lower alkyl group, $R^2$ represents a hydrogen atom or an acyl group and A represents a hydrogen atom or a tetrazolyl protective group, which comprises reacting an N-benzylthiadiazoline derivative represented by the following formula (3):

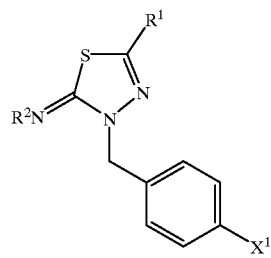
(3)

wherein $R^1$ and $R^2$ have the same meanings as defined above and $X^1$ represents a halogen atom or an acid salt of the derivative with a compound represented by the following formula (4):

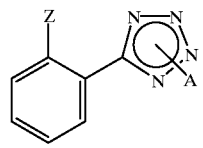
(4)

wherein Z represents a hydrogen atom, a copper atom, a lithium atom, a halogenated metal or a group $-B(OR^4)_2$ in which $R^4$ represents a hydrogen atom or a lower alkyl group, and A represents a hydrogen atom or a tetrazolyl protective group.

4. A process for producing an N-biphenylmethyl-thiadiazoline derivative represented by the following formula (7):

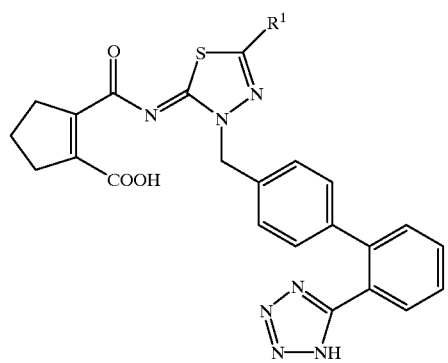
(7)

wherein $R^1$ represents a lower alkyl group or a salt thereof, which comprises reacting an N-benzylthiadiazoline derivative represented by the following formula (3):

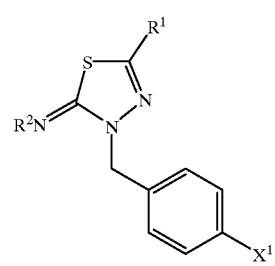
(3)

wherein $R^1$ has the same meaning as defined above, $R^2$ represents a hydrogen atom or an acyl group and $X^1$ represents a halogen atom or an acid salt thereof with a compound represented by the following formula (4):

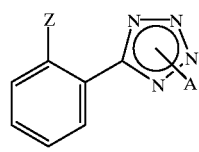
(4)

wherein Z represents a hydrogen atom, a copper atom, a lithium atom, a halogenated metal or a group —B(OR$^4$)$_2$ in which R$^4$ represents a hydrogen atom or a lower alkyl group and A represents a hydrogen atom or a tetrazolyl protective group, eliminating an acyl group in the case where the compound so obtained has the acyl group, obtaining the compound represented by the following formula (5b):

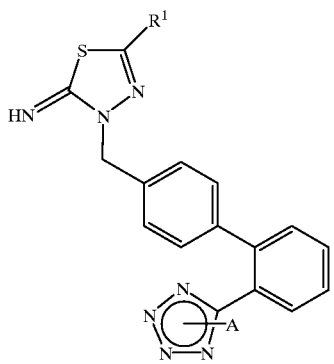

(5b)

wherein R$^1$ and A have the same meanings as defined above, reacting the compound (5b) with the compound represented by the following formula (6):

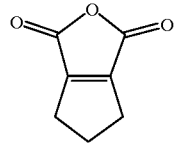

(6)

and then eliminating the tetrazolyl protective group as needed.

5. The N-benzylthiadiazoline derivative of claim 1, wherein R$^2$ represents a hydrogen atom.

6. The N-benzylthiadiazoline derivative of claim 1, wherein R$^2$ represents an acyl group.

7. The N-benzylthiadiazoline derivative of claim 6, wherein the acyl group is selected from the group consisting of lower alkanoyl, halo-lower alkanoyl, hydroxy-lower alkanoyl, alkoxy-lower alkanoyl, cyano-lower alkanoyl, lower alkenoyl, lower alkoxycarbonyl, and lower aralkyloxycarbonyl.

8. The process of claim 2, wherein R$^2$ represents a hydrogen atom.

9. The process of claim 2, wherein R$^2$ represents an acyl group.

10. The process of claim 9, wherein the acyl group is selected from the group consisting of lower alkanoyl, halo-lower alkanoyl, hydroxy-lower alkanoyl, alkoxy-lower alkanoyl, cyano-lower alkanoyl, lower alkenoyl, lower alkoxycarbonyl, and lower aralkyloxycarbonyl.

* * * * *